(12) United States Patent
Kanekasu et al.

(10) Patent No.: US 8,231,529 B2
(45) Date of Patent: Jul. 31, 2012

(54) ARM STRUCTURE AND HOLDING DEVICE FOR SURGICAL INSTRUMENT

(75) Inventors: Koichi Kanekasu, Toyama (JP); Koshi Nambu, Toyama (JP); Hiroshi Hisakado, Toyama (JP); Toshiki Nakata, Ishikawa (JP); Masakuni Arita, Ishikawa (JP); Osamu Murosaki, Toyama (JP)

(73) Assignee: Coco Inc., Ishikawa (JP)

( * ) Notice: Subject to any disclaimer, the term of this patent is extended or adjusted under 35 U.S.C. 154(b) by 263 days.

(21) Appl. No.: 12/694,127

(22) Filed: Jan. 26, 2010

(65) Prior Publication Data

US 2010/0292542 A1 Nov. 18, 2010

(30) Foreign Application Priority Data

May 15, 2009 (JP) .................................. 2009-119044

(51) Int. Cl.
*A61B 1/32* (2006.01)
(52) U.S. Cl. ........................................ 600/231; 600/227
(58) Field of Classification Search .................... 606/54; 600/201–246
See application file for complete search history.

(56) References Cited

U.S. PATENT DOCUMENTS 7,507,240 B2 * 3/2009 Olsen ................................ 606/59

FOREIGN PATENT DOCUMENTS

JP 2004-290518 A 10/2004

* cited by examiner

*Primary Examiner* — Eduardo C Robert
*Assistant Examiner* — Christina Negrelli
(74) *Attorney, Agent, or Firm* — Arent Fox LLP

(57) ABSTRACT

An arm structure includes: a pair of arms; a support post; a support member; a cam provided in one of the pair of arms; a shaft member inserted through a lateral insertion hole of the support member; and a pair of ring-shaped members provided in end portions of the shaft member, wherein by turning the one of the arms around its axis thereby to make the cam revolve, a force works to make the shaft member move, and due to its reaction force the ring-shaped members pressure-contact the support member and a slit portion is narrowed. As a result, a longitudinal insertion hole is diameter-reduced and becomes in a state of pressure-contacting the support post, leading to restriction of rotation of the arm around the support post, and the cam pressure contacts the one of the arms, leading to restriction of sliding of the arm in a long side direction, and the ring-shaped members pressure-contact the support member, leading to restriction of rotation of the arm by the shaft member.

11 Claims, 17 Drawing Sheets

F I G. 1
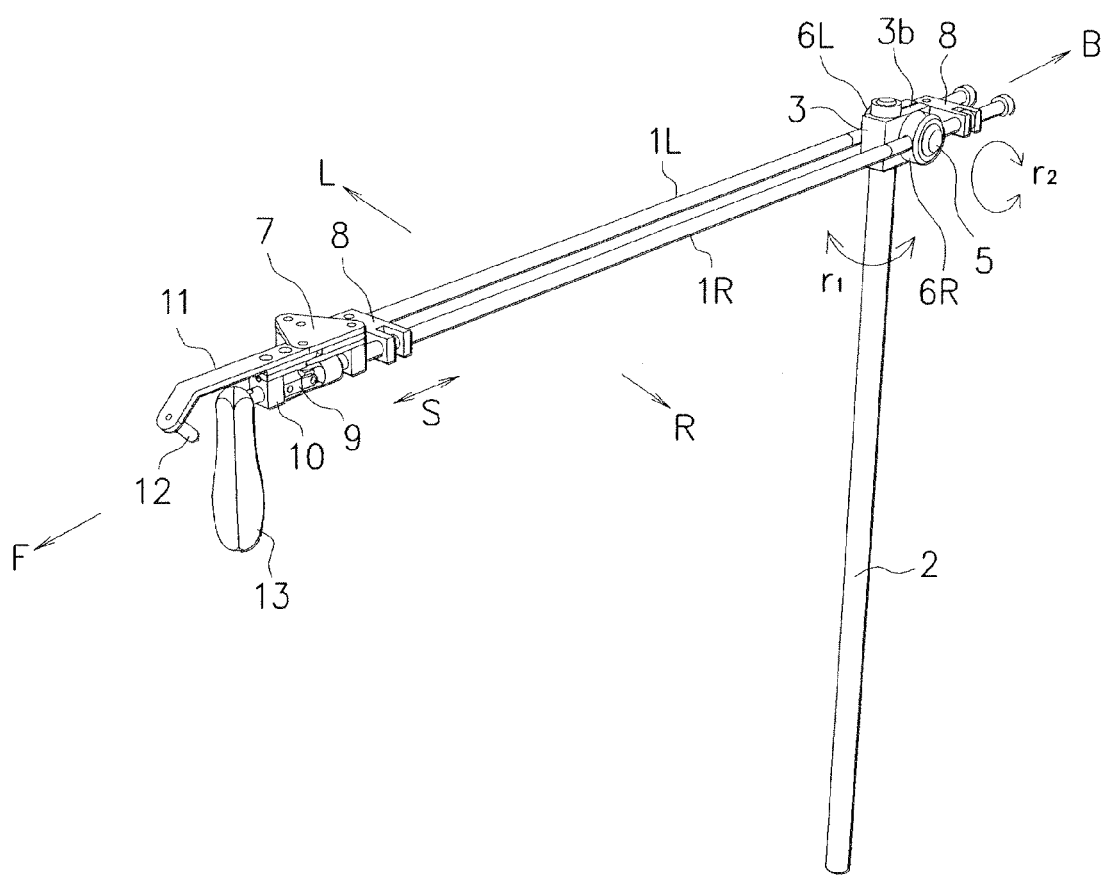

F I G. 7A
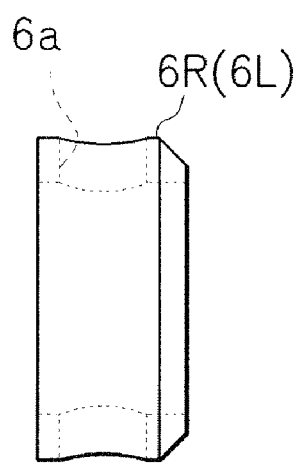
F I G. 7B
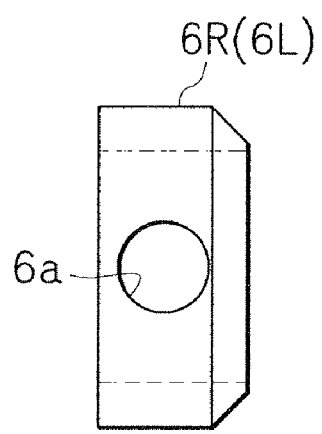
F I G. 7C
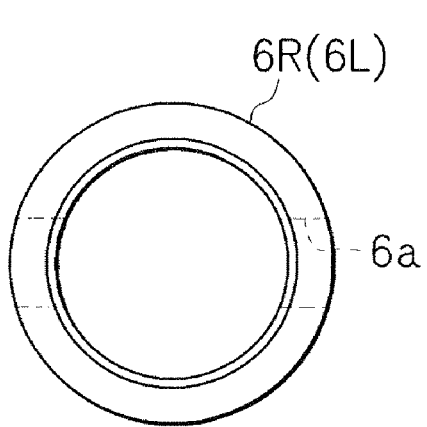

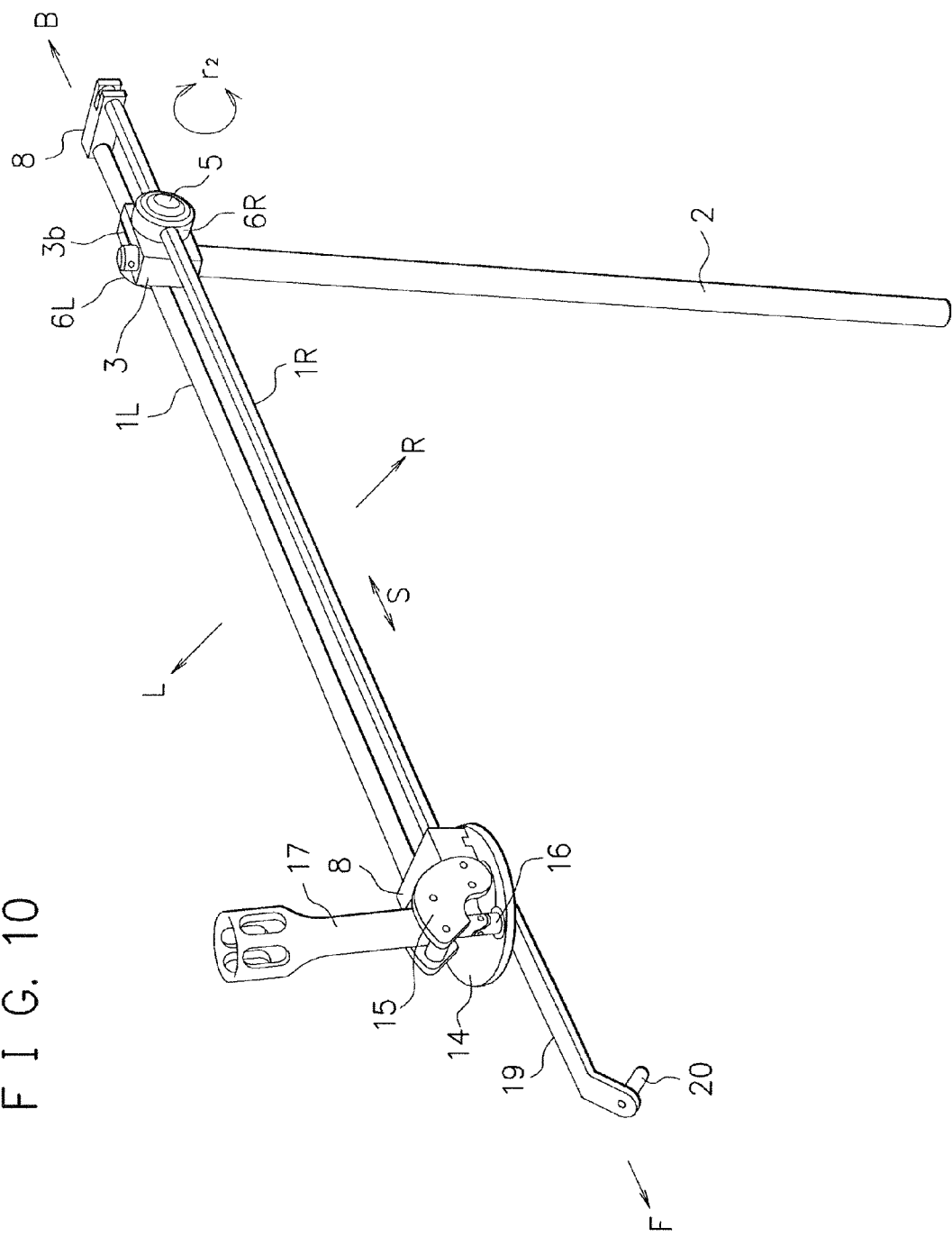

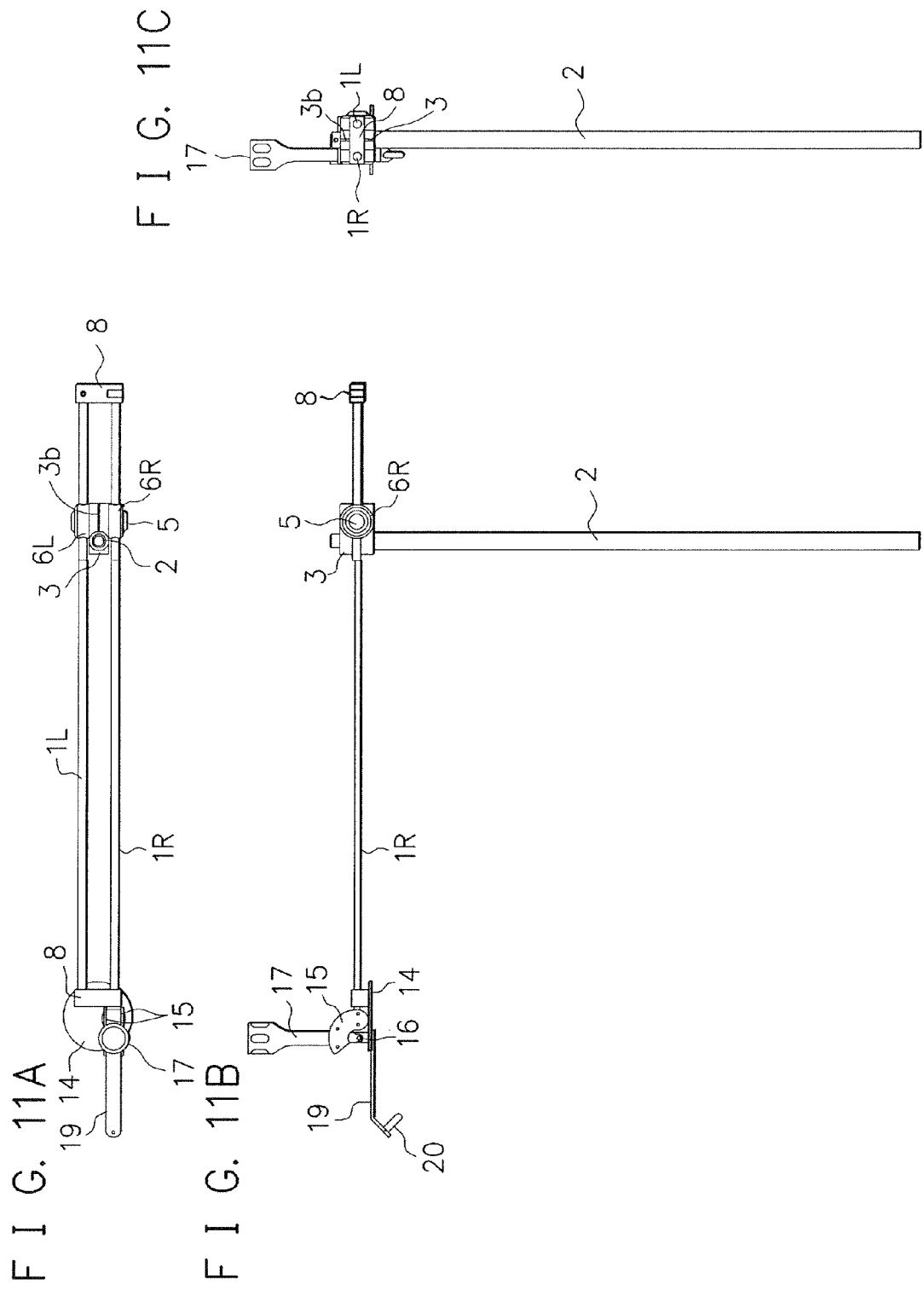

F I G. 15A
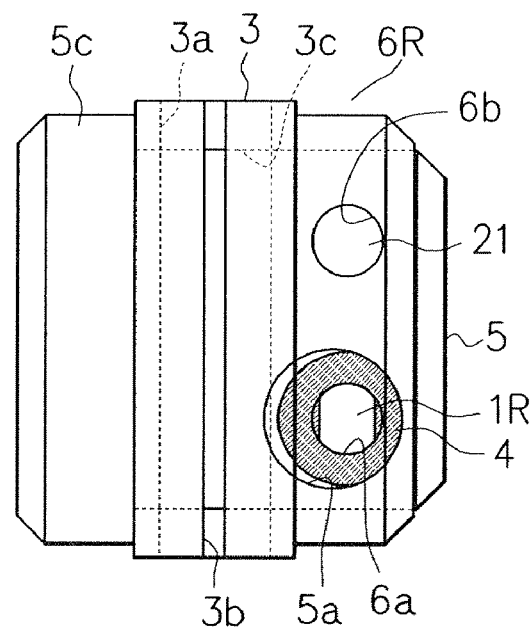
F I G. 15B
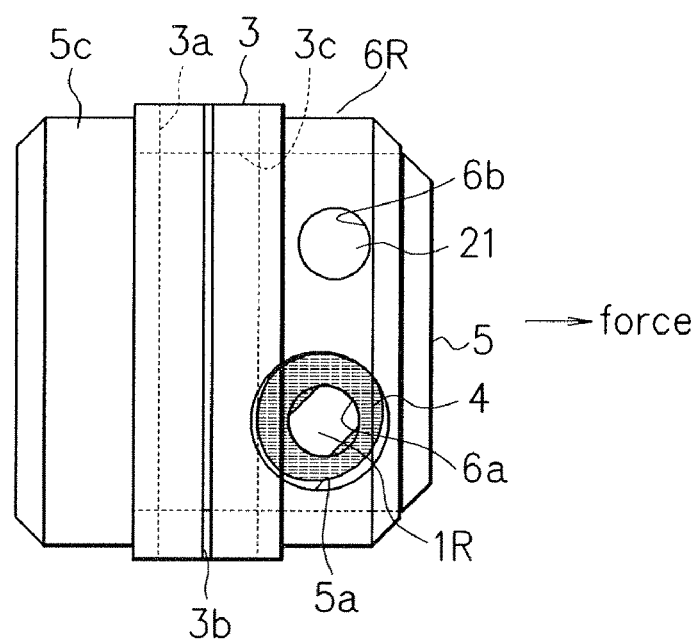

ARM STRUCTURE AND HOLDING DEVICE FOR SURGICAL INSTRUMENT

CROSS-REFERENCE TO RELATED APPLICATIONS

This application is based upon and claims the benefit of priority of the prior Japanese Patent Application No. 2009-119044, filed on May 15, 2009, the entire contents of which are incorporated herein by reference.

BACKGROUND OF THE INVENTION

1. Field of the Invention

The present invention relates to an arm structure in which an arm can be moved in a plurality of directions and each movement thereof can be locked, and to a holding device for a surgical instrument using that arm structure.

2. Description of the Related Art

In a surgical operation, a retractor 51 as shown in FIG. 17 for example is used. The retractor 51 is a surgical instrument for securing an operative field by inserting a tip thereof into an incision thereby to widen the incision. Usually, an assistant holds the retractor 51 or the retractor 51 is fixed by lacing a string through an opening 52 in a rear end.

However, if the assistant holds the retractor 51, there is a need to secure a staff for holding. Further, when the retractor 51 is desired to be moved, a surgical operator needs to give a detailed oral instruction. In a case that the retractor 51 is fixed by the string or the like, if the retractor 51 is desired to be moved, it is necessary to loosen the string once and to fix the retractor 51 again, taking a lot of trouble.

[Patent Document 1] Japanese Patent Application Laid-open No. 2004-290518

As a technique of this kind, there is disclosed in Patent Document 1 for example a device for mounting an attachment (for example, a suction unit for sucking and holding up a heart or a fork-shaped unit for pressing a pericardium (cardiac muscle surface) by two points across an anastomotic region) on a tip of an flexible arm. The flexible arm includes a flexible tube having a balled joint, a wire running inside the flexible tube. It is structured so that in a state that the wire is loosened, that is, in a state that the flexible tube can be bent freely, a position of the attachment is adjusted and in that state a handle is turned thereby to pull the wire, whereby a shape of the flexible tube is fixed by a tension of the wire, so that the position of the attachment is fixed.

However, in the flexible arm disclosed in Patent Document 1, an action to adjust the position of the attachment by bending the flexible tube and a handle manipulation for fixing and releasing of the shape of the flexible tube are separate actions.

Under the circumstances, an arm structure is desired in which a surgical instrument such as a retractor is held at a tip portion of an arm as well as the arm can be moved in a plurality of directions and each movement of the arm can be locked by a manipulation at hand. Further, such an arm structure is considered to be usable not only in a medical field but also in many other fields.

SUMMARY OF THE INVENTION

The present invention is made in view of the above problems and an object of the present invention is to provide an arm structure in which an arm can be moved in a plurality of directions and each movement of the arm can be locked by a manipulation at hand.

An arm structure according to the present invention includes a constitution in which sliding of a bar-shaped arm in a long side direction, rotation of the arm around a vertical axis, and rotation of the arm around a horizontal axis are allowed, and each movement of the arm is locked by turning the arm around its axis.

An arm structure according to the present invention includes: a support member in which a longitudinal insertion hole through which a support post is inserted longitudinally, a slit portion communicating with the longitudinal insertion hole for an entire length, and a lateral insertion hole penetrating the support member laterally through the slit portion are formed; a shaft member inserted through the lateral insertion hole of the support member; at least one bar-shaped arm inserted through an insertion hole formed in the shaft member; and a cam provided in the arm, the cam being slidable in a long side direction of the arm and revolving integrally with the arm, wherein it is constituted so that by turning the arm around its axis thereby to make the cam revolve, the slit portion of the support member is narrowed thereby to diameter-reduce the longitudinal insertion hole, leading to restriction of rotation of the arm around the support post, and restriction of sliding of the arm in the long side direction of the arm and of rotation of the arm by the shaft member.

An arm structure according to the present invention includes: a pair of parallelly disposed bar-shaped arms; a support post disposed between the pair of arms; a support member in which a longitudinal insertion hole through which the support post is inserted longitudinally, a slit portion communicating with the longitudinal insertion hole for an entire length, and a lateral insertion hole penetrating the support member laterally through the slit portion are formed; a cam provided in one of the pair of arms, the cam being slidable in a long side direction of the arm and revolving integrally with the arm; a shaft member inserted through the lateral insertion hole of the support member, in the shaft member an insertion hole through which the one of the arms is inserted in one side of the support member in a manner that the cam fitted in and an insertion hole through which the other of the arms is inserted in the other side of the support member being formed; a ring-shaped member fitted around one end portion of the shaft member, in the ring-shaped member an insertion hole through which the one of the arms is inserted being formed; and a ring-shaped member fitted around the other end portion of the shaft member, in the ring-shaped member an insertion hole through which the other of the arms is inserted being formed, wherein it is constituted so that by turning the one of the arms around its axis thereby to make the cam revolve, a force works on the shaft member in a direction of one axis, and due to its reaction force the ring-shaped member pressure-contacts the support member and the slit portion is narrowed thereby to diameter-reduce the longitudinal insertion hole, leading to restriction of rotation of the arm around the support post, and the cam pressure-contacts the one of the arms, leading to restriction of sliding of the arm in the long side direction, and the ring-shaped member pressure-contacts the support member, leading to restriction of rotation of the arm by the shaft member.

An arm structure according to the present invention includes: a bar-shaped arm; a support post; a support member in which a longitudinal insertion hole through which the support post is inserted longitudinally, a slit portion communicating with the longitudinal insertion hole for an entire length, and a lateral insertion hole penetrating the support member laterally through the slit portion are formed; a cam provided in the arm, the cam being slidable in a long side direction of the arm and revolving integrally with the arm; a shaft member inserted through the lateral insertion hole of the support member, the shaft member having an insertion hole through which the arm is inserted in one side of the support member in a manner that the cam is fitted in and a head portion positioned in the other side of the support member; and a ring-shaped member fitted around one end portion of the shaft member, in the ring-shaped member an insertion hole through which the arm is inserted being formed, wherein it is constituted so that by turning the arm around its axis thereby to make the cam revolve, a force works on the shaft member in a direction of one axis, and due to its reaction force the ring-shaped member pressure-contacts the support member and the slit portion is narrowed thereby to diameter-reduce the longitudinal insertion hole, leading to restriction of rotation of the arm around the support post, and the cam pressure-contacts the arm, leading to restriction of sliding of the arm in the long side direction, and the ring-shaped member pressure-contacts the support member, leading to restriction of rotation of the arm by the shaft member.

A cam mechanism according to the present invention includes a cam slidable in a long side direction of an arm and revolving integrally with the arm.

A holding device for a surgical instrument according to the present invention includes: the arm structure according to the present invention; a holding portion for a surgical instrument, the holding portion provided in a tip portion of the arm; and a manipulation member provided in the tip portion of the arm.

BRIEF DESCRIPTION OF THE DRAWINGS

FIG. 1 is a perspective view showing an overall constitution of an arm structure according to a first embodiment;

FIG. 7A is a plan view showing a ring-shaped member;

FIG. 7B is a front view showing the ring-shaped member;

FIG. 7C is a right side view showing the ring-shaped member;

FIG. 10 is a perspective view showing an overall constitution of an arm structure according to a second embodiment;

FIG. 11A is a plan view showing the overall constitution of the arm structure according to the second embodiment;

FIG. 11B is a right side view showing the overall constitution of the arm structure according to the second embodiment;

FIG. 11C is a rear view showing the overall constitution of the arm structure according to the second embodiment;

FIG. 15A is a view showing a substantial part of an arm structure according to a fifth embodiment and is a view for explaining an unlocked state;

FIG. 15B is a view showing the substantial part of the arm structure according to the fifth embodiment and is a view for explaining a locked state;

DETAILED DESCRIPTION OF THE PREFERRED EMBODIMENTS

Figure 2:
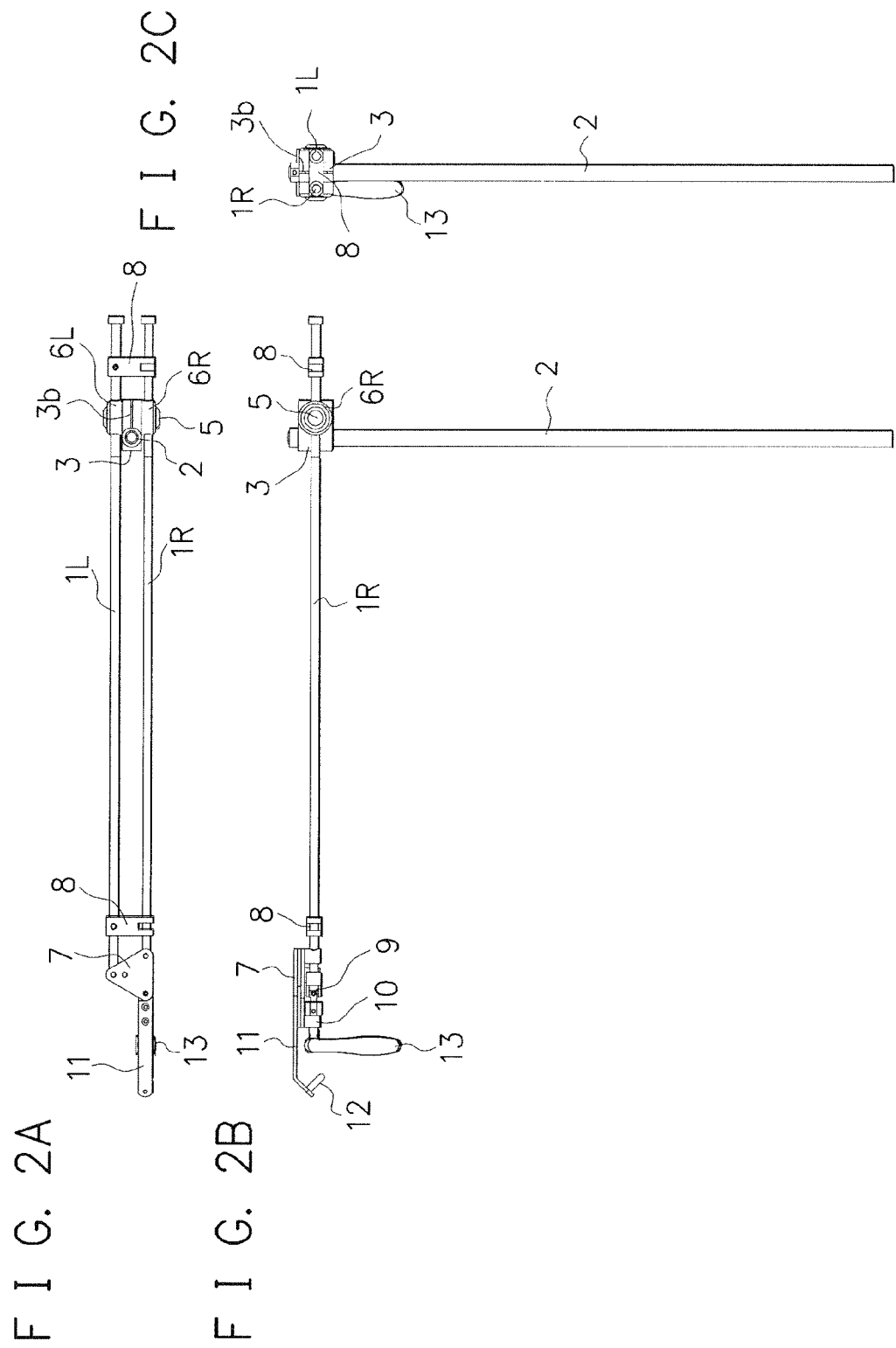
FIG. 2A is a plan view showing the overall constitution of the arm structure according to the first embodiment.
FIG. 2B is a right side view showing the overall constitution of the arm structure according to the first embodiment.
FIG. 2C is a rear view showing the overall constitution of the arm structure according to the first embodiment.
Figure 3:
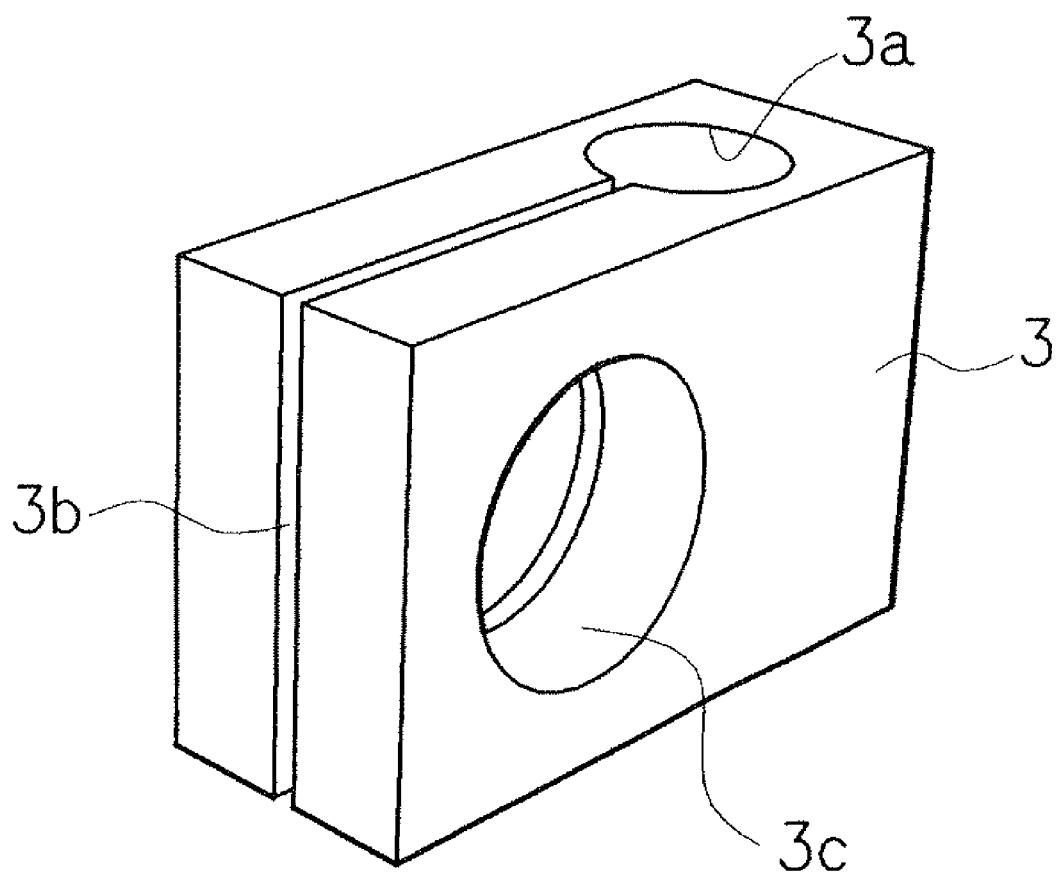
FIG. 3 is a perspective view of a support member.
Figure 4A:
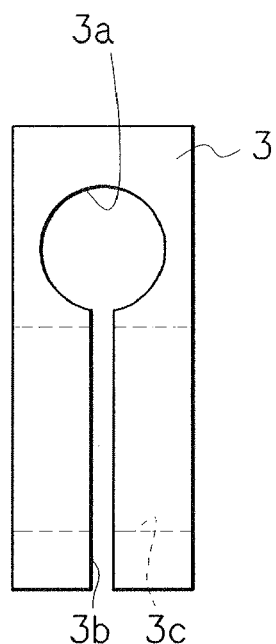
FIG. 4A is a plan view showing the support member.
Figure 4B:
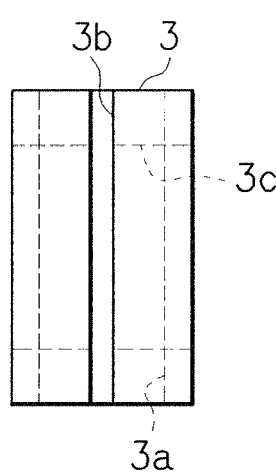
FIG. 4B is a front view showing the support member.
Figure 4C:
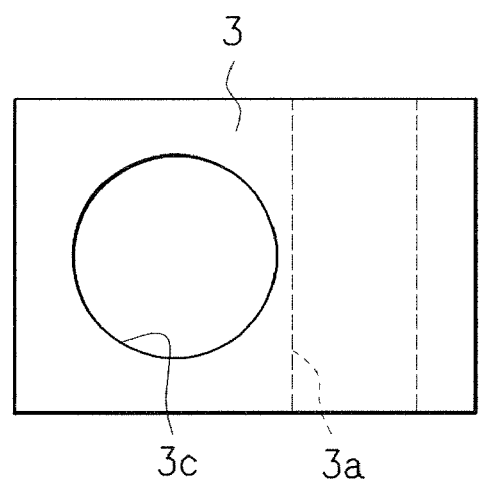
FIG. 4C is a right/left side view showing the support member.

Hereinafter, preferred embodiments of the present invention will be described with reference to the attached drawings. In the present specification, description will be done with an arrow F in FIG. 1 indicating a front, an arrow B indicating a rear, an arrow R indicating the right, and an arrow L indicating the left.

(First Embodiment)

FIG. 1 and FIG. 2A to 2C are views showing an overall constitution of an arm structure according to a first embodiment. The arm structure according to the present embodiment includes a pair of bar-shaped arms 1R, 1L which are parallelly disposed, and between these arms 1R, 1L a support post 2 is disposed. The support post 2 is fixed on a surgical bed (not shown) or in a proper position in a neighborhood of the surgical bed.

A block-shaped support member 3 is disposed between the pair of arms 1R, 1L. FIG. 3 and FIG. 4A to FIG. 4C show the support member 3. In the support member 3 a longitudinal insertion hole 3a through which the support post 2 is longitudinally inserted is formed and the support member 3 can be rotated around the support post 2. It should be noted that the support member 3 itself is supported by another support member (not shown) provided in the support post 2. If a height level of this another support member is made to be changeable, it is also possible to alter a height level of the support member 3 appropriately. Further, a slit portion 3b communicating with the longitudinal insertion hole 3a for an entire length is formed in the support member 3, the slit portion 3b being able to be broadened/narrowed in correspondence with a force from the right and the left. Further, a lateral insertion hole 3c penetrating the support member 3 laterally through the slit portion 3b is formed in the support member 3.

Figure 5:
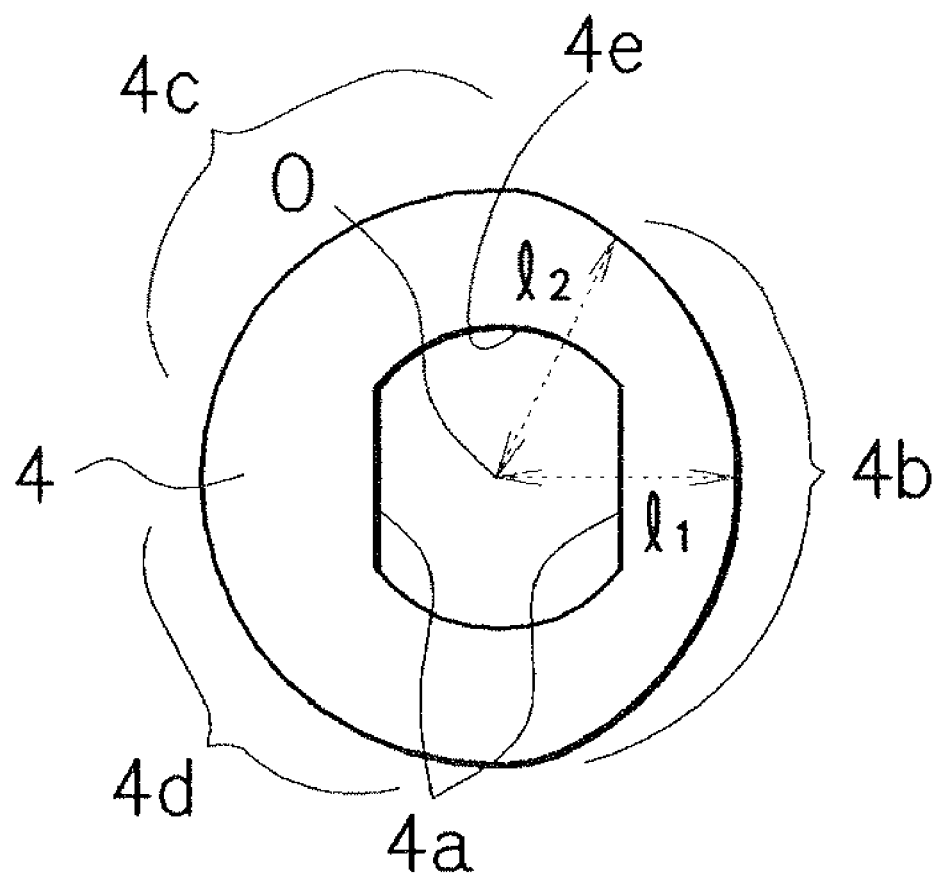
FIG. 5 is a plan view of a cam.

The arm 1R of a right side of the pair of arms 1R, 1L is provided with a cam 4. FIG. 5 shows the cam 4. The cam 4 has a ring shape through which the arm 1R is inserted. Here, two chamfers 1a are formed in the arm 1R (see FIG. 8A, FIG. 8B, FIG. 9A, FIG. 9B), and plane surface portions 4a corresponding to the chamfers 1a of the arm 1R are formed on an inner peripheral surface of the cam 4. Thereby, the cam 4 is slidable with the arm 1R being an axis in a long side direction thereof and revolves integrally with the arm 1R. It should be noted that though the two chamfers 1a and plane surface portions 4a are provided here, the number thereof can be only one, or three or more.

An outer peripheral surface of the cam 4 has a shape made by connecting three arc surfaces 4b, 4c, 4d off centered. These three arc surfaces 4b, 4c, 4d have the same curvature as that of an inner peripheral surface of an insertion hole 5a of a shaft member 5 described later. Besides, a center of a sliding hole 4e through which the arm 1R is inserted is offsetted to an arc surface 4b side.

Figure 6A:
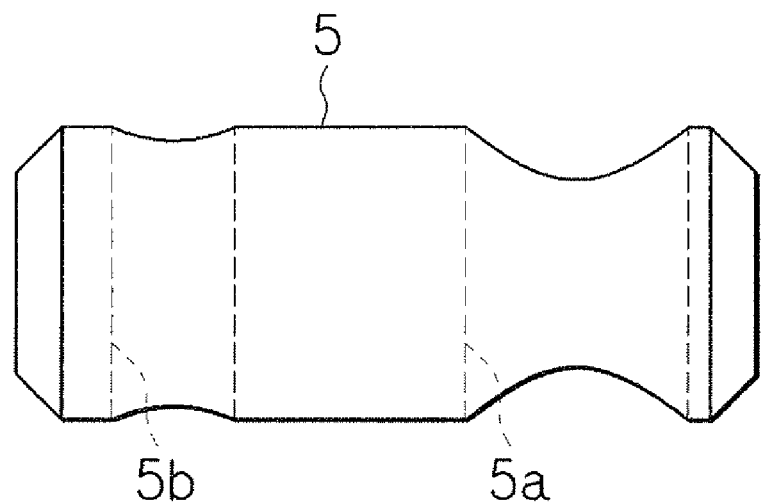
FIG. 6A is a plan view showing a shaft member.
Figure 6B:
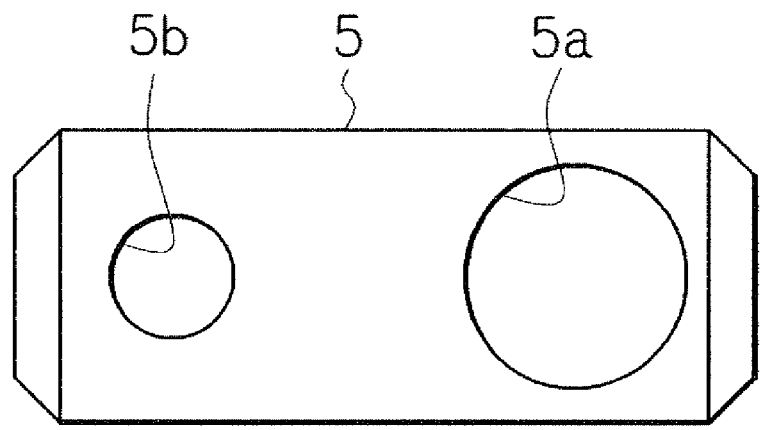
FIG. 6B is a front view showing the shaft member.

The shaft member 5 is inserted through the lateral insertion hole 3c of the support member 3. FIG. 6A and FIG. 6B show the shaft member 5. The insertion hole 5a through which the arm 1R is inserted in a right side of the support member 3 is formed in the shaft member 5 and the cam 4 is fitted in the insertion hole 5a (see FIG. 8A, FIG. 8B, FIG. 9A, FIG. 9B). Further, an insertion hole 5b through which the arm 1L is inserted in a left side of the support member 3 is formed in the shaft member 5.

A ring-shaped member 6R is fitted around a right end portion of the shaft member 5, in the right side of the support member 3. FIG. 7A to FIG. 7C show the ring-shaped member 6R. An insertion hole 6a through which the arm 1R is inserted is formed in the ring-shaped member 6R, and a size relation is that the ring-shaped member 6R abuts on a right side surface of the support member 3 in a state that the arm 1R is inserted through the insertion hole 6a (see FIG. 8A, FIG. 8B, FIG. 9A, FIG. 9B).

Similarly, in the left side of the support member 3, a ring-shaped member 6L is fitted around a left end portion of the shaft member 5. FIG. 7A to FIG. 7C show the ring-shaped member 6L. An insertion hole 6a through which the arm 1L is inserted is formed in the ring-shaped member 6L, and a size relation is that the ring-shaped member 6L abuts on a left side surface of the support member 3 in a state that the arm 1L is inserted through the insertion hole 6a (see FIG. 8A, FIG. 8B, FIG. 9A, FIG. 93).

Tip portions of the pair of arms 1R, 1L are coupled by a coupling board 7. Further, bridge members 8 are bridged between the pair of arms 1R, 1L, in fronts and rears thereof. It should be noted that the right side arm 1R can be turned around its axis.

A second arm 10 is coupled to a tip of the right side arm 1R via a universal joint 9. The second arm 10 is provided with a holding plate 11 extending forward almost horizontally. A tip portion of the holding plate 11 is bent downward, and a pin portion 12 to be inserted into a hole 52 of a retractor 51 sticks up on a lower surface of the tip portion. In a state that an incision is broadened by the retractor 51, a force works on the retractor 51 in a pulled direction (in a direction different from a slipping direction from the pin portion 12), so that the retractor 51 can be held by only the pin portion 12.

Besides, a lever 13 being a manipulation member for manipulating the arms 1R, 1L is fixed on a tip of the second arm 10.

The above-described arms 1R, 1L, cam 4, support member 3, shaft member 5, ring-shaped members 6R, 6L and the like are made of stainless steel, but are not limited thereto. For example, the cam 4 can be made of a resin having predetermined hardness, heat resistance and the like. Since the arm 1R and the cam 4 slide on each other, the resin-made cam 4 has an advantage that the arm 1R is hardly scratched.

Hereinafter, actions of the arm structure according to the present embodiment will be described also with reference to FIG. 8A, FIG. 8B, FIG. 9A, and FIG. 9B. It should be noted that in FIG. 8A, FIG. 8B, FIG. 9A, and FIG. 9B, a positional relation between the arms 1R, 1L and the slit portion 3b of the support member 3 is different from that in FIG. 1, and FIG. 2A to FIG. 2C, but it is for the sake of convenience in describing and fundamental actions are not changed. In other words, the slit portion 3b of the support member 3 can be faced backward as shown in FIG. 1 or can be faced forward as shown in FIG. 8A, FIG. 8B, FIG. 9A, FIG. 9B.

Figure 8A:
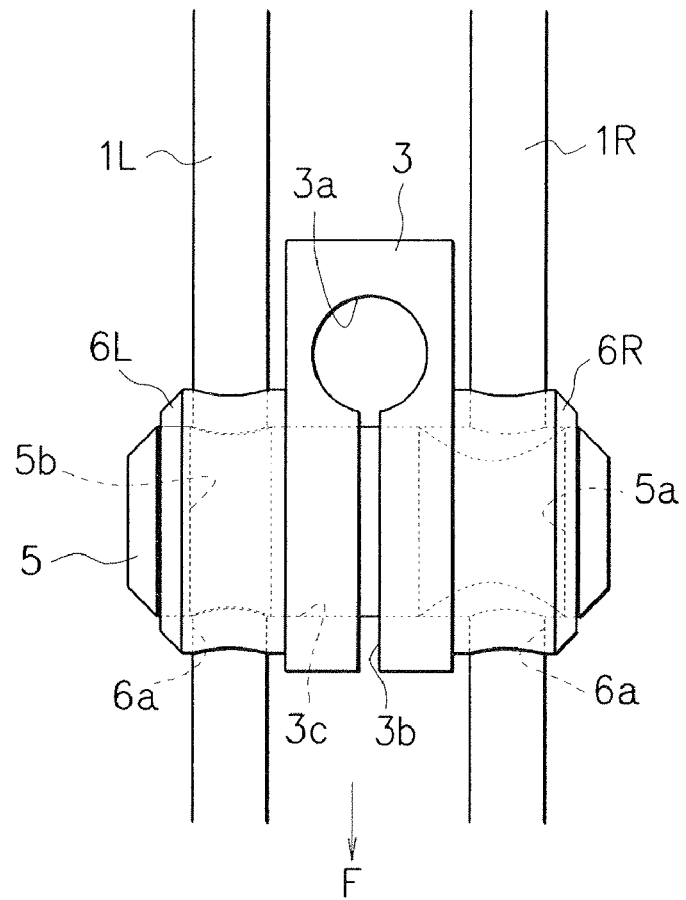
FIG. 8A and FIG. 8B are views for explaining an unlocked state of the arm structure according to the first embodiment.
Figure 8B:
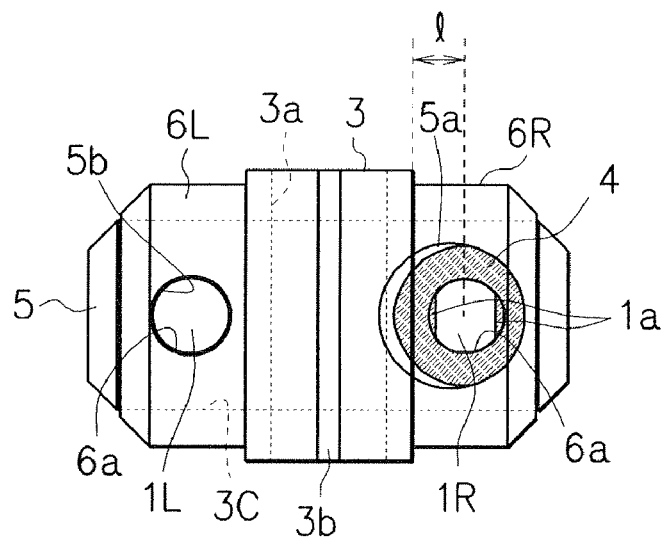

FIG. 8A and FIG. 8B show the unlocked state. In the unlocked state, as shown in FIG. 8B, the arc surface 4b of the cam 4 contacts the inner peripheral surface of the insertion hole 5a, in the insertion hole 5a of the shaft member 5.

In the unlocked state shown in FIG. 8A and FIG. 8B, as shown by an arrow S in FIG. 1, the arms 1R, 1L can be moved forward and backward (sliding of the arms 1R, 1L in the long side direction). Further, as shown by an arrow $r_1$ in FIG. 1, the arms 1R, 1L together with the support member 3 can be rotated around the support post 2 (rotation of arms 1R, 1L around a vertical axis). Further, as shown by an arrow $r_2$ in FIG. 1, the arms 1R, 1L together with the ring-shaped members 6R, 6L can be rotated by the shaft member 5 (rotation of the arms 1R, 1L around a horizontal axis). These movements are all possible by the manipulation by the lever 13.

Further, is possible to move only the second arm 10 and the holding plate 11 via the universal joint 9.

Figure 9A:
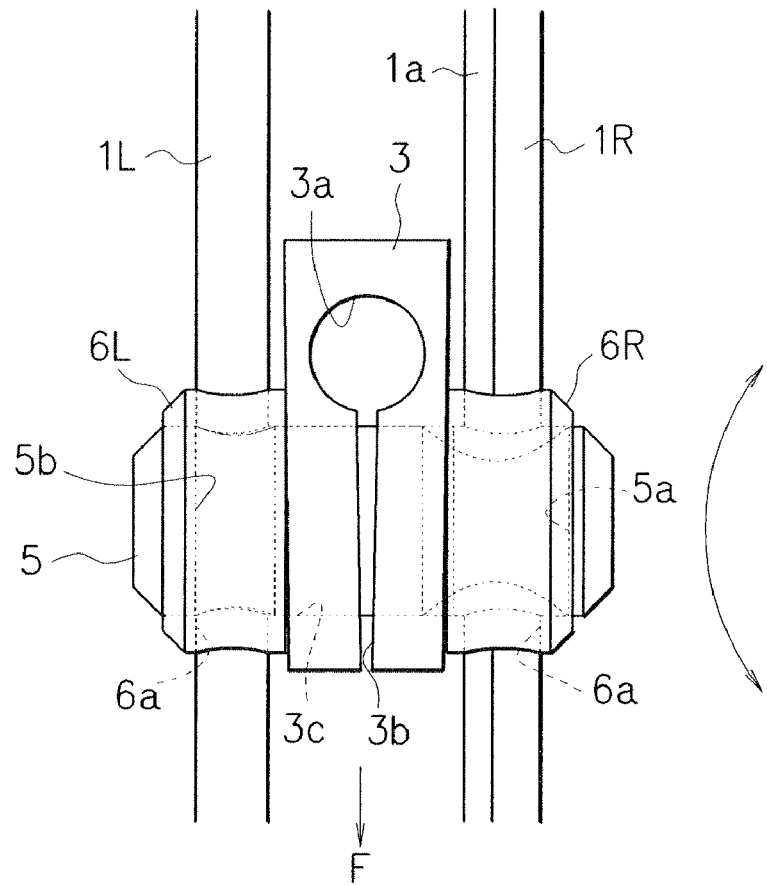
FIG. 9A and FIG. 9B are views for explaining a locked state of the arm structure according to the first embodiment.
Figure 9B:
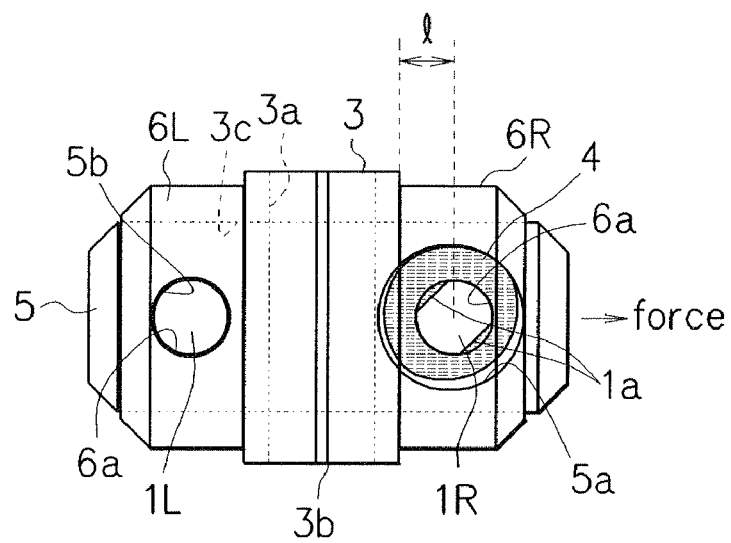

On the other hand, FIG. 9A and FIG. 9B show the locked state. When the lever 13 is manipulated to turn the right side arm 1R around its axis in a clockwise direction, the cam 4 also revolves integrally in the clockwise direction as shown in FIG. 9B. Here, as shown in FIG. 5, a revolving center O (that is, a revolving center of the cam 4) of the arm 1R is offsetted in an arc surface 4b side compared with a center (not shown) of the arc surface 4b. Thereby, in the unlocked state of FIG. 8A and FIG. 8B, a distance $l_1$ between the revolving center O of the arm 1R and the inner peripheral surface of the insertion hole 5a is short, while a distance $l_2$ between the revolving center O of the arm 1R and the inner peripheral surface of the insertion hole 5a becomes longer as the cam 4 revolves. Therefore, with revolving of the cam 4, a force (force in an arrow direction in FIG. 9B) in an axis direction works on the shaft member 5.

However, since the arm 1L is inserted through the shaft member 5, the shaft member 5 cannot move in the direction of the force. Therefore, a reaction force from the inner peripheral surface of the insertion hole 5a and the cam 4 works to narrow a distance between the arms 1R, 1L, so that the arm 1R bows (see an arrow in FIG. 9A). Here, since the ring-shaped members 6R, 6L abut on the support member 3, distances l between the support member 3 and the arms 1R, 1L are restrained by the ring-shaped members 6R, 6L. As a result, the ring-shaped members 6R, 6L pushed by the arms 1R, 1L pressure-contact the support member 3, thereby narrowing the slit portion 3b.

As described above, in the locked state of FIG. 9A and FIG. 9B, the cam 4 becomes in a state of pressure-contacting the arm 1R, so that forward and backward movement of the arms 1R, 1L (sliding in the ling side direction of the arms 1R, 1L) is restricted. Besides, the longitudinal insertion hole 3a is diameter-reduced due to narrowing of the slit portion 3b and becomes in a state of pressure-contacting the support post 2, so that rotation of the arms 1R, 1L around the support post 2 (rotation of the arms 1R, 1L around the vertical axis) is restricted. Further, the ring-shaped members 6R, 6L become in a state of pressure-contacting the support member 3, so that rotation of the arms 1R, 1L by the shaft member 5 (rotation of the arms 1R, 1L around the horizontal axis) is restricted.

It should be noted that in the locked state shown in FIG. 9A and FIG. 9B, the arc surface 4c (see FIG. 5) of the cam 4 pressure-contacts the inner peripheral surface of the insertion hole 5a, and the cam 4 (that is, the arm 1R) does not revolve in the clockwise direction any more. In the present embodiment, as described above, the outer peripheral surface of the cam 4 has a shape made by connecting three arc surfaces 4b, 4c, 4d off centered, and thereby the cam 4 and the insertion hole 5a can be made small.

Further, in the present embodiment an example in which the right side arm 1R is turned around its axis in the clockwise direction is explained, but a locked state can be similarly brought about even if the right side arm 1R is turned in a counterclockwise direction.

As described above, in the arm structure according to the present embodiment, it is constituted so that sliding of the arms 1R, 1L in the long side direction, rotation of the arms 1R, 1L around the vertical axis, and rotation of the arms 1R, L around the horizontal axis are allowed, and that each movement of the arms 1R, 1L is locked by turning the arm 1R around its axis. According to such a constitution, it is possible to move the arms 1R, 1L in plural directions and to lock each movement of the arms 1R, 1L, by a manipulation at hand.

During a surgical operation, when a surgical operator wants to move a retractor 51, the surgical operator can turn an arm 1R via a lever 13 to bring the arm 1R into an unlocked state and can continuously manipulate the lever 13 thereby to adjust a position of the retractor 51. Then, after adjusting the position of the retractor 51, the surgical operator can turn the arm 1R via the lever 13 again to bring the arm 1R into a locked state thereby to fix the retractor 51. In other words, adjustment and fixing of the position of the retractor 51 can be performed by a series of manipulations at hand.

(Second Embodiment)

FIG. 10 and FIG. 11A to FIG. 11C are views showing an overall constitution of an arm structure according to a second embodiment. The arm structure according to the second embodiment is different from that according to the above-described first embodiment only in a structure of a holding portion for a retractor 51, and a fundamental constitution of the arm structure is similar. Hereinafter, the same reference numerals and symbols are given to the components similar to those in the first embodiment, and detailed explanation thereof will be omitted.

Bridge members 8 are bridged between a pair of arms 1R, 1L in fronts and rears thereof. It should be noted that the arm 1R of a right side can be turned around its axis. The front side bridge member 8 is attached on a disk-shaped plate 14, and right and left guide plates 15 are connected to a tip of the arm 1R protruding from the bridge member 8. Further, on the plate 14, a lever 17 being a manipulation member for manipulating the arms 1R, 1L sticks up via a universal joint 16. The lever 17 is disposed between the right and left guide plates 15, and by manipulating the lever 17 the arm 1R can be turned around its axis.

A holding plate 19 extending forward almost horizontally is provided on a lower surface of the plate 14. A tip portion of the holding plate 19 is bent downward, and on a lower surface of that tip portion a pin portion 20 to be inserted into a hole 52 of a retractor 51 sticks up. In a state that an incision is broadened by the retractor 51, a force works on the retractor 51 in a pulled direction (in a direction different from a slipping direction from the pin portion 20), so that the retractor 51 can be held by only the pin portion 20.

(Third Embodiment)

Figure 12:
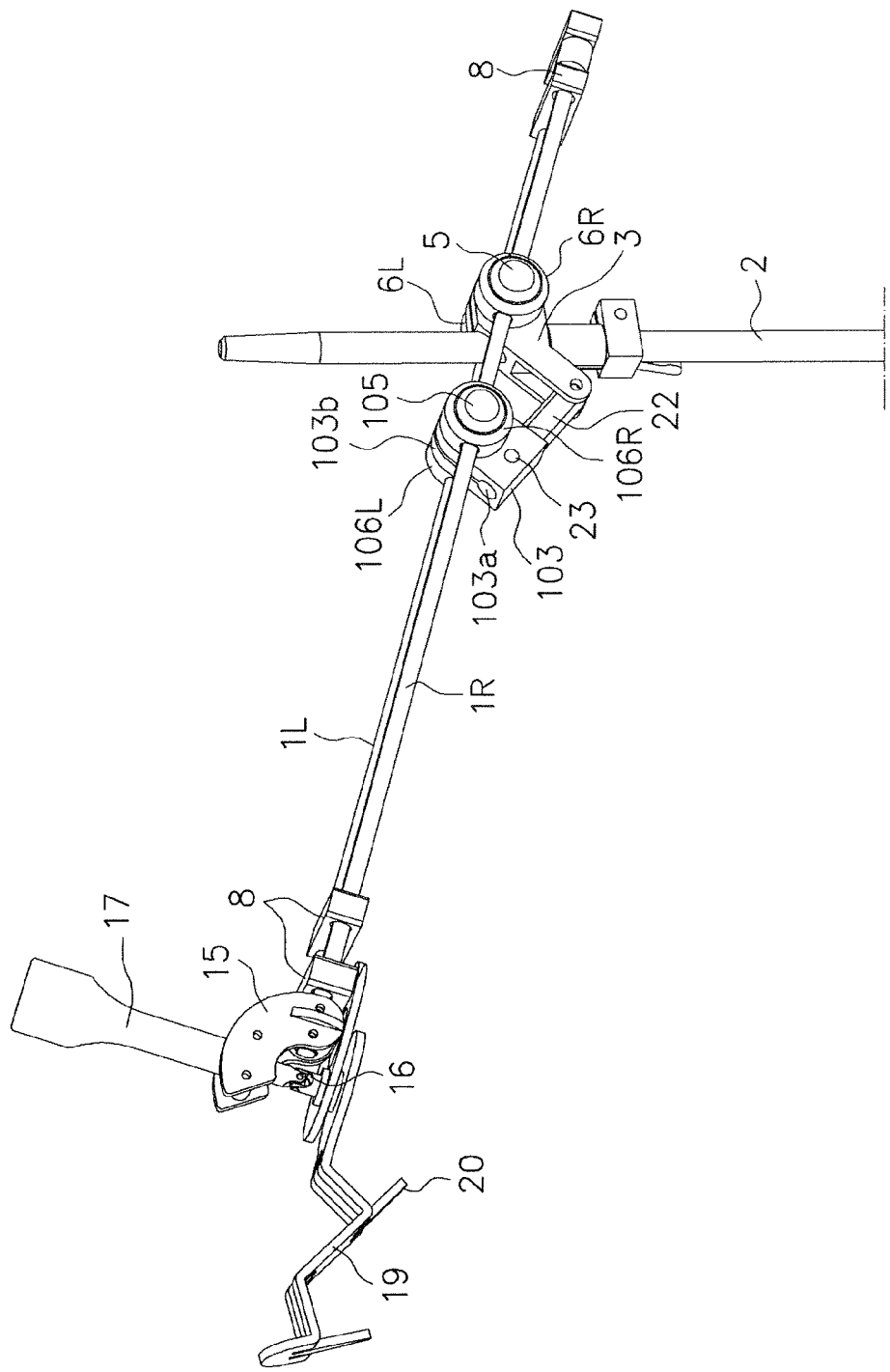
FIG. 12 is a perspective view showing an overall constitution of an arm structure according to a third embodiment.

FIG. 12 is a view showing an overall constitution of an arm structure according to a third embodiment. The arm structure according to the third embodiment is similar to that according the second embodiment described above in a fundamental constitution, except that a second support member 103 having a block shape is disposed between a pair of arms 1R, 1L in a different position from that of a support member 3. In the second support member 103, there are formed an insertion hole 103a similar to a longitudinal insertion hole 3a of the support member 3, a slit portion 103b similar to a slit portion 3b, a lateral insertion hole similar to a lateral insertion hole 3c.

Besides, the arm 1R of a right side of the pair of arms 1R, 1L is provided with a second cam similar to a cam 4 (though not shown in FIG. 12, it is referred to as a cam 104 for the sake of convenience). Further, a second shaft member 105 similar to a shaft member 5 is inserted through the second support member 103. Further, second ring-shaped members 106R, 106L similar to ring-shaped members 6R, 6L are disposed in right and left sides of the second support member 103.

The support member 3 and the second support member 103 are connected by a link member 22. In other words, one end of the link member 22 is rotatably coupled to the support member 3. Further, the other end of the link member 22 is inserted through the insertion hole of the second support member 103 and fixed by a pin 23.

Also in the arm structure according to the present embodiment, the arms 1R, 1L can be moved forward and backward (sliding of the arms 1R, 1L in a long side direction) in an unlocked state. Besides, the arms 1R, 1L together with the support member 3 can be rotated around a support post 2 (rotation of the arm 1R around a vertical axis). Further, the arms 1R, 1L together with the ring-shaped members 6R, 6L can be rotated by the shaft member 5 (rotation of the arms 1R, 1L around a horizontal axis). When the arms 1R, 1L are rotated by the shaft member 5, the second ring-shaped member 106R, 106L revolve and the link member 22 continued to the second support member 103 is rotated in relation to the first support member 3, enabling the second support member 103 to approach the support member 3 or to get apart from the support member 3, so that rotation of the arms 1R, 1L around a horizontal axis and sliding of the arms 1R, 1L in a long side direction are not restricted.

In order to change from the unlocked state to a locked state, the arm 1R is turned around its axis in a clockwise direction, causing thereby the cam 4 and also the second cam 104 to revolve integrally in the clockwise direction, and a force in the axis direction works on the shaft member 5 and the second shaft member 105 similarly to the way described in the first embodiment.

However, since the arm 1L is inserted through the shaft member 5 and the second shaft member 105, the shaft member 5 and the second shaft member 105 are unmovable in a direction of the force. Therefore, due to a reaction force from an inner peripheral surface of the insertion hole 5a of the shaft member 5 and the cam 4 as well as a reaction force from an inner peripheral surface of the insertion hole of the second shaft member 105 and the second cam 104, the arm 1R bows. Here, since the ring-shaped member 6R, 6L abut on the support member 3 and the second ring-shaped members 106R, 106L abut on the second support member 103, distances between the support member 3 and the second support member 103, and the arms 1R, 1L are constrained by the ring-shaped members 6R, 6L and the second ring-shaped members 106R, 106L respectively. As a result, the ring-shaped members 6R, 6L and the second ring-shaped members 106R, 106L which are pushed by the arms 1R, 1L pressure-contact the support member 3 and the second support member 103 respectively, thereby narrowing the slit portion 3b of the support member 3 and the slit portion 103b of the second support member 103.

As described above, in the locked state, the cam 4 and the second cam 104 become in a state of pressure-contacting the arm 1R, whereby forward and backward movement of the arms 1R, 1L (sliding of the arms 1R, 1L in a long side direction) is restricted. Further, in the support member 3, due to narrowing the slit portion 3b the longitudinal insertion hole 3a is diameter-reduced and becomes in a state of pressure-contacting the support post 2, so that rotation of the arms 1R, 1L around the support post 2 (rotation of the arms 1R, 1L around the vertical axis) is restricted. Further, also in the second support member 103, due to narrowing of the slit portion 103b the insertion hole 103a is diameter-reduced and becomes in a state of pressure-contacting the other end of the link member 22. Further, the ring-shaped members 6R, 6L become in a state of pressure-contacting the support member 3, so that rotation of the arms 1R, 1L by the shaft member 5 (rotation of the arms 1R, 1L around the horizontal axis) is restricted.

In a case of the present embodiment, in the locked state, as shown in FIG. 12, the arms 1R, 1L, the support member 3 as well as the second support member 103, and the link member 22 combine to make a truss, so that rotation of the arms 1R, 1L around the horizontal axis in particular is restricted more firmly. In this case, if the second support member 103 does not have the insertion hole 103a or a diameter of the insertion hole 103a is larger than a diameter of the link member 22 for example, flexibility of bowing of the arm 1R is increased and a force to constraint is weakened, so that a firm truss structure cannot be realized.

(Fourth Embodiment)

In the first to third embodiments described above, examples in which the arm structure has a pair of arms 1R, 1L are explained, but as shown in FIG. 13A, FIG. 13B, FIG. 14A, and FIG. 14B a constitution is possible in which an arm structure has only one arm 1R. Hereinafter, differences from the first embodiment will be illustrated and explained, and the same reference numerals and symbols are given to components similar to those in the first embodiment, and detailed explanation thereof will be omitted.

A shaft member 5 is inserted through a lateral insertion hole 3c of a support member 3. The shaft member 5 is bar-shaped in the above-described first embodiment, while in the present embodiment the shaft member 5 is of a shape having an integrally formed large-diameter head portion 5c on one end.

Similarly to the first embodiment, an insertion hole 5a through which the arm 1R is inserted in a right side of the support member 3 is formed in the shaft member 5, and a cam 4 is fitted in the insertion hole 5a and a ring-shaped member 6R is fitted around a right end portion of the shaft member 5 in the right side of the support member 3. An insertion hole 6a through which the arm 1R is inserted is formed in the ring-shaped member 6R, and a size relation is that the ring-shaped member 6R abuts on a right side surface of the support member 3 in a state that the arm 1R is inserted through the insertion hole 6a.

Besides, in the present embodiment, a size relation is that a head portion 5c of the shaft member 5 abuts on a left side surface of the support member 3 in a left side of the support member 3.

Figure 13A:
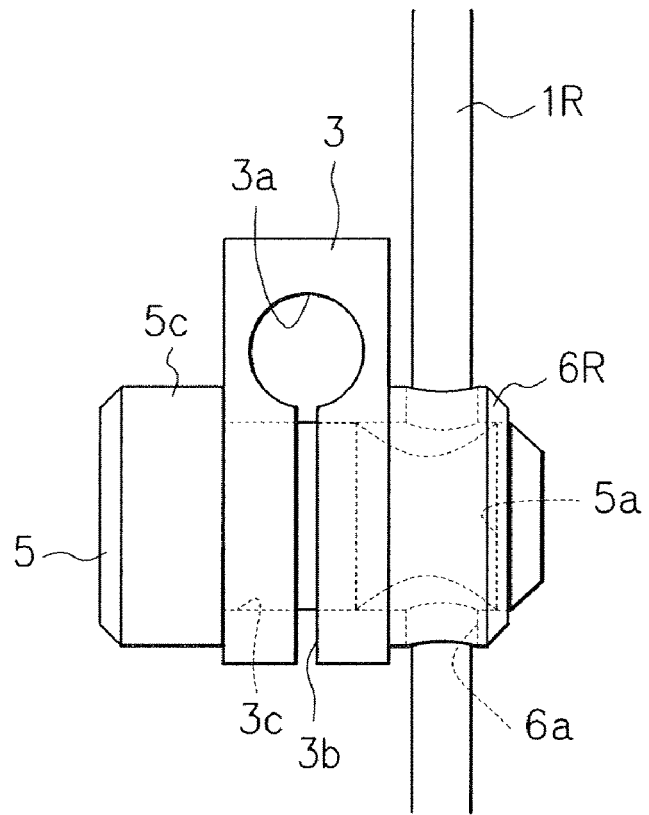
FIG. 13A and FIG. 13B are views for explaining an unlocked state of an arm structure according to a fourth embodiment.
Figure 13B:
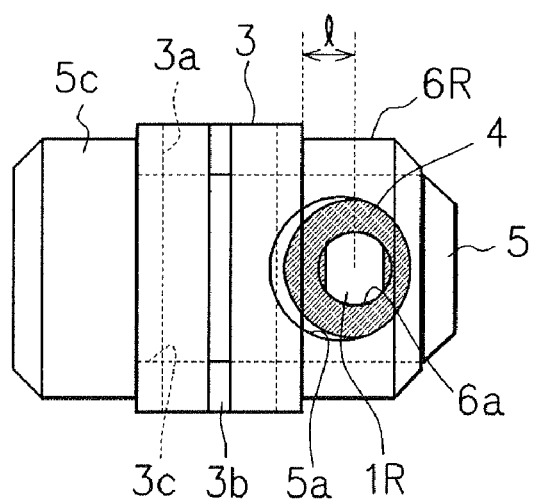

FIG. 13A and FIG. 13B show an unlocked state. In the unlocked state, as shown in FIG. 13B, an arc surface 4b of the cam 4 contacts an inner peripheral surface of the insertion hole 5a, in the insertion hole 5a of the shaft member 5.

In the unlocked state shown in FIG. 13A and FIG. 13B, the arm 1R can be moved forward and backward (sliding of the arm 1R in a long side direction). Besides, the arm 1R together with the support member 3 can be rotated around a support post 2 (rotation of the arm 1R around a vertical axis). Further, the arm 1R together with the ring-shaped member 6R can be rotated by the shaft member 5 (rotation of the arm 1R around a horizontal axis).

Figure 14A:
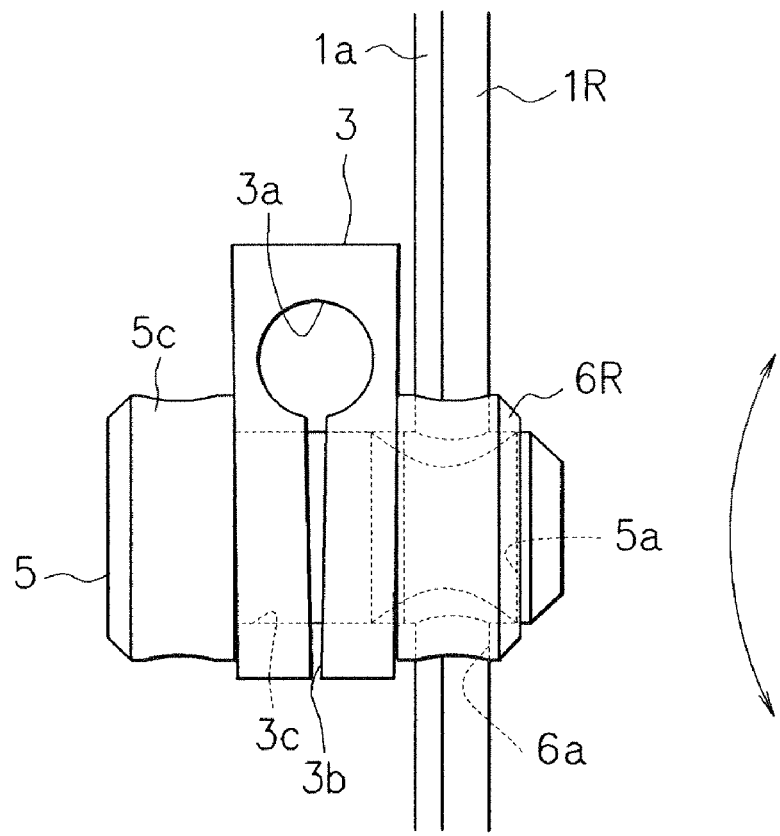
FIG. 14A and FIG. 14B are views for explaining a locked state of the arm structure according to the fourth embodiment.
Figure 14B:
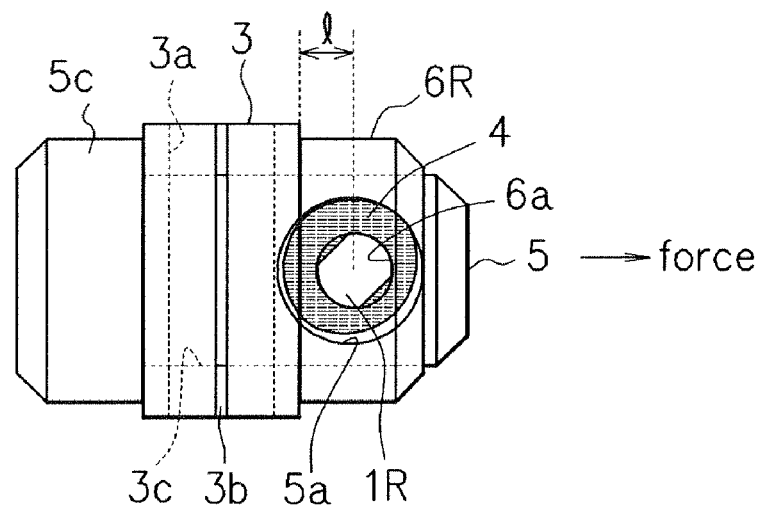

On the other hand, FIG. 14A and FIG. 14B show a locked state. When the arm 1R is turned around its axis in a clockwise direction, the cam 4 also revolves integrally in the clockwise direction as shown in FIG. 14B, and a force in an axis direction (force in an arrow direction in FIG. 9B) works on the shaft member 5 as described in the first embodiment.

However, since the head portion 5c of the shaft member 5 abuts on a left side surface of the support member 3, the shaft member 5 is unmovable in a direction of the force. Therefore, due to a reaction force from an inner peripheral surface of the insertion hole 5a and the cam 4, the arm 1R bows (see an arrow in FIG. 14A). Here, since the ring-shaped member 6R abuts on the support member 3, a distance 1 between the support member 3 and the arm 1R is constrained by the ring-shaped member 6R. As a result, the ring-shaped member 6R pushed by the arm 1R pressure-contacts the support member 3, thereby narrowing a slit portion 3b.

As described above, in the locked state of FIG. 14A and FIG. 14B, the cam 4 becomes in a state of pressure-contacting the arm 1R, so that forward and backward movement of the arm 1R (sliding of the arm 1R in the long side direction) is restricted. Further, due to narrowing of the slit portion 3 the longitudinal insertion hole 3a is diameter-reduced and becomes in a state of pressure-contacting the support post 2, so that rotation of the arm 1R around the support post 2 (rotation of the arm 1R around the vertical axis) is restricted. Further, the ring-shaped member 6R becomes in a state of pressure-contacting the support member 3, so that rotation of the arm 1R by the shaft member 5 (rotation of the arm 1R around the horizontal axis) is restricted.

It should be noted that a second support member 103 as described in the third embodiment can be provided also in the case of the constitution of only one arm 1R as in the present embodiment. In this case, a second shaft member 105 can have a head portion to abut on a left side surface of the second support member 103.

(Fifth Embodiment)

FIG. 15A and FIG. 15B are views showing substantial parts of an arm structure according to a fifth embodiment. The arm structure according to the fifth embodiment is similar to the arm structure according the third embodiment described above in a fundamental constitution, except that an arm 21 is provided in addition to an arm 1R. The arm 21 for reinforcement is provided in correspondence with an object to be held by a tip of the arm 1R.

As shown in FIG. 15A and FIG. 15E, in a shaft member 5 an insertion hole 5a through which the arm 1R is inserted is formed in a right side of a support member 3, and a cam 4 is fitted in this insertion hole 5a. Further, an insertion hole through which the arm 21 is inserted in the right side of the support member 3 is formed in the shaft member 5.

In the right side of the support member 3, a ring-shaped member 6R is fitted around a right end portion of the shaft member 5. An insertion hole 6a through which the arm 1R is inserted and an insertion hole 6b through which the arm 21 is inserted are formed in the ring-shaped member 6R, and a size relation is that the ring-shaped member 6R abuts on a right side surface of the support member 3 in a state that the arms 1R, 21 are inserted into the insertion holes 6a, 6b.

Further, similarly to the third embodiment, a size relation is that a head portion 5c of the shaft member 5 abuts on a left side surface of the support member 3 in a left side of the support member 3.

(Other Embodiments)

Preferred embodiments in carrying out the present invention are described hereinabove, but the present invention is not limited to only those embodiments and alteration is possible within a range to realize the present invention. For example, another embodiment is shown FIG. 16A and FIG.

16B. It should be noted that in description the same reference numerals and symbols are given to components similar to those in the first embodiment.

A pair of arms 1R, 1L, a support post 2, and a support member 3 are similar to those of the first embodiment, but a cam 4 is not fitted in an insertion hole 5a of a shaft member 5 which penetrates the support member 3, only the arm 1R being inserted therethrough. Further, the arm 1L is disposed in a manner that a gap is not generated with a left side surface of the support member 3.

The right side arm 1R is provided with a cam 4 slidable in a long side direction of the arm 1R and having a predetermined shape which revolves integrally with the arm 1R, the cam 4 abutting on one surface of the support member 3. It should be noted that though not shown in FIG. 16A or FIG. 16B, movement of the cam 4 in the long side direction of the arm 1R is restricted by a stopper or the like disposed on a side surface of the support member for example.

In the case of the present embodiment, the arm 1R is turned around its axis to make the cam 4 revolve, and the cam 4 directly applies a force to the support member 3, thereby narrowing a slit portion 3b. As a result, a longitudinal insertion hole 3a is diameter-reduced and rotation of the arms 1R, 1L around the support post 2 is restricted. Further, due to a reaction force from the support member 3 side, the can 4 becomes in a state of pressure-contacting the arm 1R, so that sliding of the arms 1R, 1L in the long side direction is restricted. Further, the cam 4 becomes in a state of pressure-contacting the support member 3, so that rotation of the arm 1R, 1L by the shaft member 5 is restricted.

Figure 16A:
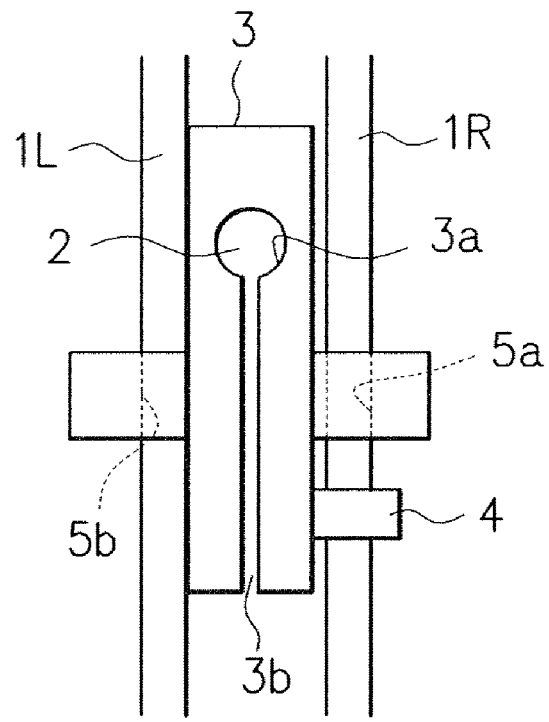
FIG. 16A and FIG. 16B are views for explaining an arm structure according to another embodiment.
Figure 16B:
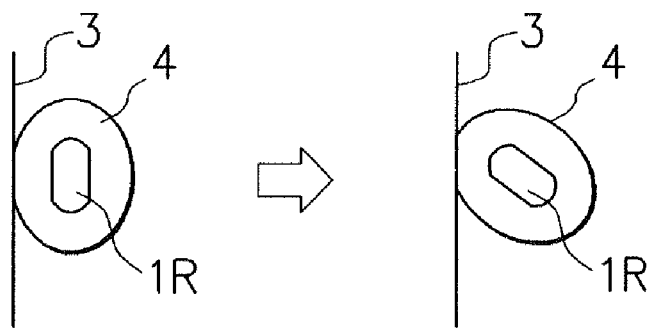
Figure 17:
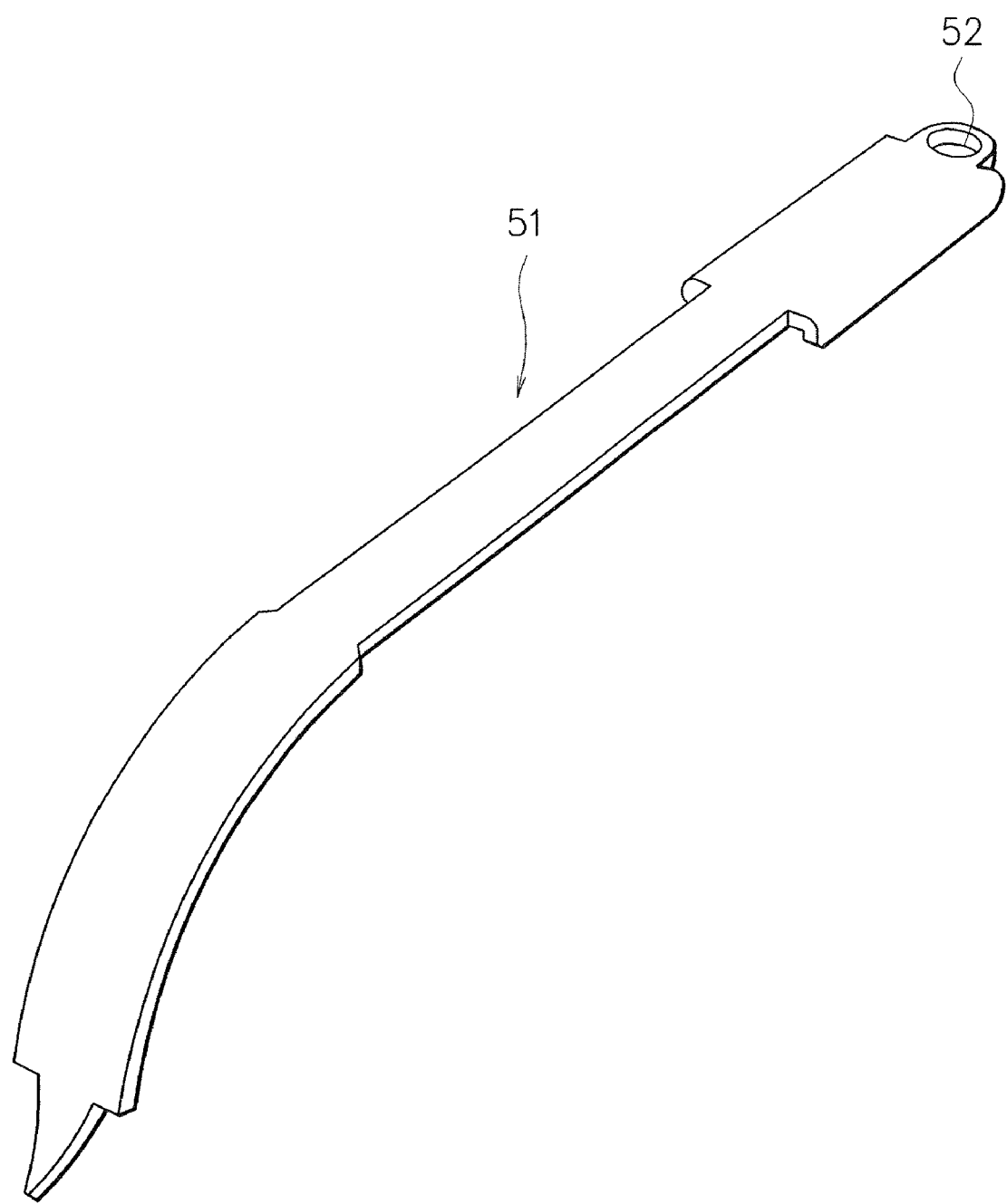
FIG. 17 is a perspective view of a retractor.

Also in the case of an example shown by FIG. 16A and FIG. 16B, it can be constituted so that only an arm 1 R is provided and a shaft member 5 has a head portion 5c abutting on a left side surface of the support member 3 as described in the fourth embodiment.

In the above-described embodiments, the arm structure used for a holding device for a surgical instrument such as a retractor is described, but the arm structure of the present invention is also applicable in other technology field, such as to a robot arm and an arm of a lighting apparatus and the like for example.

According to the present invention, it is possible to provide an arm structure in which an arm can be moved in a plurality of directions and each movement of the arm can be locked by a manipulation at hand.

The present embodiments are to be considered in all respects as illustrative and no restrictive, and all changes which come within the meaning and range of equivalency of the claims are therefore intended to be embraced therein. The invention may be embodied in other specific forms without departing from the spirit or essential characteristics thereof.

What is claimed is:

1. An arm structure comprising:
   a support member in which a longitudinal insertion hole through which a support post is inserted longitudinally, a slit portion communicating with the longitudinal insertion hole for an entire length, and a lateral insertion hole penetrating said support member laterally through the slit portion are formed;
   a shaft member inserted through the lateral insertion hole of said support member;
   at least one bar-shaped arm inserted through an insertion hole formed in said shaft member; and
   a cam provided in said arm, said cam being slidable in a long side direction of said arm and revolving integrally with said arm, wherein
   it is constituted so that by turning said arm around its axis thereby to make said cam revolve, the slit portion of said support member is narrowed thereby to diameter-reduce the longitudinal insertion hole, leading to restriction of rotation of said arm around the support post, and restriction of sliding of said arm in the long side direction of said arm and of rotation of said arm by said shaft member.

2. The arm structure according to claim 1, wherein said cam has a ring shape through which said arm is inserted and a chamfer is formed in said arm, and a plan surface corresponding to the chamfer is formed in an inner peripheral surface of said cam.

3. An arm structure comprising:
   a pair of parallelly disposed bar-shaped arms;
   a support post disposed between said pair of arms;
   a support member in which a longitudinal insertion hole through which said support post is inserted longitudinally, a slit portion communicating with the longitudinal insertion hole for an entire length, and a lateral insertion hole penetrating said support member laterally through the slit portion are formed;
   a cam provided in one of said pair of arms, said cam being slidable in a long side direction of said arm and revolving integrally with said arm;
   a shaft member inserted through the lateral insertion hole of said support member, in said shaft member an insertion hole through which the one of said arms is inserted in one side of said support member in a manner that said cam is fitted in and an insertion hole through which the other of said arms is inserted in the other side of said support member being formed;
   a ring-shaped member fitted around one end portion of said shaft member, in said ring-shaped member an insertion hole through which the one of said arms is inserted being formed; and
   a ring-shaped member fitted around the other end portion of said shaft member, said ring-shaped member an insertion hole through which the other of said arms is inserted being formed, wherein
   it is constituted so that by turning the one of said arms around its axis thereby to make said cam revolve, a force works on said shaft member in a direction of one axis, and due to its reaction force said ring-shaped member pressure-contacts said support member and the slit portion is narrowed thereby to diameter-reduce the longitudinal insertion hole, leading to restriction of rotation of said arm around said support post, and said cam pressure-contacts the one of said arms, leading to restriction of sliding of said arm in the long side direction, and said ring-shaped member pressure-contacts said support member, leading to restriction of rotation of said arm by said shaft member.

4. The arm structure according to claim 3, wherein said cam has a ring shape through which the one of said arms is inserted and a chamfer is formed in said arm, and a plan surface portion corresponding to the chamfer is formed in an inner peripheral surface of said cam.

5. The arm structure according to claim 3, comprising:
   a second support member in which an insertion hole, a slit portion communicating with the insertion hole for an entire length, and a lateral insertion hole penetrating said second support member laterally through the slit portion are formed;
   a second cam provided in the one of said arms, said second cam being slidable in the long side direction of said arm and revolving integrally with said arm;

a second shaft member inserted through the lateral insertion hole of said second support member, in said second shaft member an insertion hole through which the one of said arms is inserted in one side of said second support member in a manner that said second cam is fitted in and an insertion hole through which the other of said arms is inserted in the other side of said second support member being formed;

a second ring-shaped member fitted around one end portion of said second shaft member, in said second ring-shaped member an insertion hole through which the one of said arms is inserted being formed;

a second ring-shaped member fitted around the other end portion of said second shaft member, in said second ring-shaped member an insertion hole through which the other of said arms is inserted being formed; and a link member one end of which is rotatably connected to said support member and the other end of which is fixed in a state of being inserted through the insertion hole of said second support member.

6. An arm structure comprising:
a bar-shaped arm;
a support post;
a support member in which a longitudinal insertion hole through which said support post is inserted longitudinally, a slit portion communicating with the longitudinal insertion hole for an entire length, and a lateral insertion hole penetrating said support member laterally through the slit portion are formed;
a cam provided in said arm, said cam being slidable in a long side direction of said arm and revolving integrally with said arm;
a shaft member inserted through the lateral insertion hole of said support member, said shaft member having an insertion hole through which said arm is inserted in one side of said support member in a manner that said cam is fitted in and a head portion positioned in the other side of said support member; and
a ring-shaped member fitted around one end portion of said shaft member, in said ring-shaped member an insertion hole through which said arm is inserted being formed, wherein
it is constituted so that by turning said arm around its axis thereby to make said cam revolve, force works on said shaft member in a direction of one axis, and due to its reaction force said ring-shaped member pressure-contacts said support member and the slit portion is narrowed thereby to diameter-reduce the longitudinal insertion hole, leading to restriction of rotation of said arm around said support post, and said cam pressure-contacts said arm, leading to restriction of sliding of said arm in the long side direction, and said ring-shaped member pressure-contacts said support member, leading to restriction of rotation of said arm by said shaft member.

7. The arm structure according to claim 6, wherein said cam has a ring shape through which said arm is inserted and a chamfer is formed in said arm, and a plan surface portion corresponding to the chamfer is formed in an inner peripheral surface of said cam.

8. The arm structure according to claim 6, comprising:
a second support member in which an insertion hole, a slit portion communicating with the insertion hole for an entire length, and a lateral insertion hole penetrating said second support member laterally through the slit portion are formed;

a second cam provided in said arm, said second cam being slidable in the long side direction of said arm and revolving integrally with said arm;

a second shaft member inserted through the lateral insertion hole of said second support member, said second shaft member having an insertion hole through which said arm is inserted in one side of said second support member a manner that said second cam is fitted in and a head portion positioned in the other side of said second support member;

a second ring-shaped member fitted around one end portion of said second shaft member, in said second ring-shaped member an insertion hole through which said arm is inserted being formed; and a link member one end of which is rotatably connected to said support member and the other end of which is fixed in a state of being inserted through the insertion hole of said second support member.

9. A holding device for a surgical instrument, comprising:
an arm structure including:
a support member in which a longitudinal insertion hole through which a support post is inserted longitudinally, a slit portion communicating with the longitudinal insertion hole for an entire length, and a lateral insertion hole penetrating said support member laterally through the slit portion are formed;
a shaft member inserted through the lateral insertion hole of said support member;
at least one bar-shaped arm inserted through an insertion hole formed in said shaft member; and
a cam provided in said arm, said cam being slidable in a long side direction of said arm and revolving integrally with said arm, wherein
it is constituted so that by turning said arm around its axis thereby to make said cam revolve, the slit portion of said support member is narrowed thereby to diameter-reduce the longitudinal insertion hole, leading to restriction of rotation of said arm around the support post, and restriction of sliding of said arm in the long side direction of said arm and of rotation of said arm by said shaft member,
a holding portion for a surgical instrument, said holding portion provided in a tip portion of said arm; and
a manipulation member provided in the tip portion of said arm.

10. A holding device for a surgical instrument, comprising:
an arm structure including:
a pair of parallelly disposed bar-shaped arms; a support post disposed between said pair of arms;
a support member in which a longitudinal insertion hole through which said support post is inserted longitudinally, a slit portion communicating with the longitudinal insertion hole for an entire length, and a lateral insertion hole penetrating said support member laterally through the slit portion are formed;
a cam provided in one of said pair of arms, said cam being slidable in a long side direction of said arm and revolving integrally with said arm;
a shaft member inserted through the lateral insertion hole of said support member, in said shaft member an insertion hole through which the one of said arms is inserted in one side of said support member in a manner that said cam is fitted in and an insertion hole through which the other of said arms is inserted in the other side of said support member being formed;
a ring-shaped member fitted around one end portion of said shaft member, in said ring-shaped member an insertion hole through which the one of said arms is inserted being formed; and a ring-shaped member fitted around the other end portion of said shaft member, in said ring-shaped member an insertion hole through which the other of said arms is inserted being formed, wherein it is constituted so that by turning the one of said arms around its axis thereby to make said cam revolve, a force works on said shaft member in a direction of one axis, and due to its reaction force said ring-shaped member pressure-contacts said support member and the slit portion is narrowed thereby to diameter-reduce the longitudinal insertion hole, leading to restriction of rotation of said arm around said support post, and said cam pressure-contacts the one of said arms, leading to restriction of sliding of said arm in the long side direction, and said ring-shaped member pressure-contacts said support member, leading to restriction of rotation of said arm by said shaft member, a holding portion for a surgical instrument, said holding portion provided in a tip portion of said arm; and a manipulation member provided in the tip portion of the one of said arms.

11. A holding device for a surgical instrument, comprising:
an arm structure including:
  a bar-shaped arm;
  a support post;
  a support member in which a longitudinal insertion hole through which said support post is inserted longitudinally, a slit portion communicating with the longitudinal insertion hole for an entire length, and a lateral insertion hole penetrating said support member laterally through the slit portion are formed;

a cam provided in said arm, said cam being slidable in a long side direction of said arm and revolving integrally with said arm; a shaft member inserted through the lateral insertion hole of said support member, said shaft member having an insertion hole through which said arm is inserted in one side of said support member in a manner that said cam is fitted in and a head portion positioned in the other side of said support member; and a ring-shaped member fitted around one end portion of said shaft member, in said ring-shaped member an insertion hole through which said arm is inserted being formed, wherein it is constituted so that by turning said arm around its axis thereby to make said cam revolve, a force works on said shaft member in a direction of one axis, and due to its reaction force said ring-shaped member pressure-contacts said support member and the slit portion is narrowed thereby to diameter-reduce the longitudinal insertion hole, leading to restriction of rotation of said arm around said support post, and said cam pressure-contacts said arm, leading to restriction of sliding of said arm in the long side direction, and said ring-shaped member pressure-contacts said support member, leading to restriction of rotation of said arm by said shaft member, a holding portion for a surgical instrument, said holding portion provided in a tip portion of said arm; and a manipulation member provided in the tip portion of said arm.

\* \* \* \* \*